(12) United States Patent
Brisimi et al.

(10) Patent No.: US 11,194,784 B2
(45) Date of Patent: Dec. 7, 2021

(54) EXTRACTING STRUCTURED INFORMATION FROM UNSTRUCTURED DATA USING DOMAIN PROBLEM APPLICATION VALIDATION

(71) Applicant: International Business Machines Corporation, Armonk, NY (US)

(72) Inventors: Theodora Brisimi, Dublin (IE); Spyros Kotoulas, Dublin (IE); Vanessa Lopez Garcia, Dublin (IE); Valentina Rho, Dublin (IE); Natalia Mulligan, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 262 days.

(21) Appl. No.: 16/165,620

(22) Filed: Oct. 19, 2018

(65) Prior Publication Data
US 2020/0125659 A1 Apr. 23, 2020

(51) Int. Cl.
*G06F 16/23* (2019.01)
*G06N 20/00* (2019.01)
*G06F 16/25* (2019.01)

(52) U.S. Cl.
CPC ........ *G06F 16/2365* (2019.01); *G06F 16/254* (2019.01); *G06N 20/00* (2019.01)

(58) Field of Classification Search
CPC .... G06F 16/2365; G06F 16/254; G06N 20/00
See application file for complete search history.

(56) References Cited

U.S. PATENT DOCUMENTS 7,739,133 B1 6/2010 Hail et al.
7,747,495 B2 6/2010 Malaney et al.
(Continued)

OTHER PUBLICATIONS

Albert, et al., "Representing Domain Knowledge by Concept Maps: How to Validate Them?," 2nd Joint Workshop of Cognition and Learning Through Media-Communication for Advanced e-Learning (JWCL), 2005, Tokyo, Japan, 7 pages, 2005.
(Continued)

*Primary Examiner* — Miranda Le
(74) *Attorney, Agent, or Firm* — Amin, Turocy & Watson, LLP

(57) ABSTRACT

Techniques are described for extracting structured information from unstructured documents based on validation of the structured information as applied to a domain problem associated with the unstructured documents. In one embodiment, a computer program product for automated information extraction is provided. The computer program product comprising a computer readable storage medium having program executable by a processing component to cause the processing component to extract structured candidate interpretations of a rule from unstructured information that defines a plurality of rules intended to control operations of a system, and determine measures of validity of the structured candidate interpretations based on application of the candidate policy interpretations to historical operational data for the system that represents operations performed by the system. The measures of validity respectively can represent degrees to which the historical operational data reflects operation of the system in accordance with the structured candidate interpretations.

20 Claims, 10 Drawing Sheets

(56) References Cited

U.S. PATENT DOCUMENTS

| | | | |
|---|---|---|---|
| 7,917,378 B2* | 3/2011 | Fitzgerald | G06Q 50/22 705/4 |
| 8,099,736 B2* | 1/2012 | Hoerle | G06F 9/546 719/313 |
| 8,438,047 B2* | 5/2013 | Curtin | G06Q 10/10 705/4 |
| 8,666,787 B2* | 3/2014 | Lesswing | G06Q 40/04 705/4 |
| 9,299,108 B2 | 3/2016 | Diana et al. | |
| 9,721,315 B2* | 8/2017 | Christen | G06Q 50/22 |
| 2003/0208379 A1* | 11/2003 | Haskey | G06Q 50/22 705/2 |
| 2005/0234740 A1 | 10/2005 | Krishnan et al. | |
| 2009/0048877 A1* | 2/2009 | Binns | G06Q 10/04 705/4 |
| 2010/0145734 A1* | 6/2010 | Becerra | G06Q 10/087 705/4 |
| 2010/0305977 A1 | 12/2010 | Hogan et al. | |
| 2011/0161106 A1* | 6/2011 | Chapman | G06Q 40/02 705/2 |
| 2011/0246229 A1 | 10/2011 | Pacha | |
| 2013/0054259 A1* | 2/2013 | Wojtusiak | G06Q 10/10 705/2 |
| 2014/0149128 A1* | 5/2014 | Getchius | G06Q 10/10 705/2 |
| 2014/0297336 A1* | 10/2014 | Hoerle | G06Q 40/00 705/4 |
| 2016/0239923 A1* | 8/2016 | Phillips | G06Q 40/08 |
| 2016/0379309 A1 | 12/2016 | Shikhare | |
| 2020/0285997 A1* | 9/2020 | Bhattacharyya | G06N 20/00 |

OTHER PUBLICATIONS

Gomes, et al., "Information Extraction in the Business Intelligence Context," Aug. 28, 2010, 23 pages.

Chandola, et al., "Knowledge discovery from massive healthcare claims data," KDD '13 Proceedings of the 19th ACM SIGKDD international conference on Knowledge discovery and data mining, Chicago, Illinois, USA—Aug. 11-14, 2013, 2 pages.

Saggion, et al., "Ontology-based Information Extraction for Business Intelligence," Last Accessed: Jun. 19, 2018, 14 pages.

Joudaki, et al., "Using Data Mining to Detect Health Care Fraud and Abuse: A Review of Literature," Glob J Health Sci. Jan. 2015; 7(1): 194-202, Published online Aug. 31, 2014. doi: 10.5539/gjhs.v7n1p194, 12 pages.

\* cited by examiner

EXTRACTING STRUCTURED INFORMATION FROM UNSTRUCTURED DATA USING DOMAIN PROBLEM APPLICATION VALIDATION

TECHNICAL FIELD

This application relates to techniques for extracting structured information from unstructured documents based on validation of the structured information as applied to a domain problem associated with the unstructured documents.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments described herein, systems, computer-implemented methods, apparatus and/or computer program products are presented that provide techniques for extracting structured information from unstructured documents based on validation of the structured information as applied to a domain problem associated with the unstructured documents.

According to one or more embodiments of the present invention, a device can comprise a memory that stores computer executable components and a processor that executes the computer executable components stored in the memory. The computer executable components can comprise an extraction component that extracts structured candidate interpretations of a rule from unstructured information that defines a plurality of rules intended to control operations of a system. The computer executable components can further comprise a validation component that determines measures of validity of the structured candidate interpretations based on application of the candidate policy interpretations to historical operational data for the system that represents operations performed by the system. For example, the measures of validity can respectively represent degrees to which the historical operational data reflects operation of the system in accordance with the structured candidate interpretations.

In various embodiments, computer executable components can further comprise a rule evaluation component that selects one or more structured candidate interpretations of the structured candidate interpretations as accurate interpretations of the rule based on the measures of validity of the structured candidate interpretations, thereby ensuring the one or more candidate interpretations are consistent with actual operations of the system. The rule evaluation component can select the one or more structured candidate interpretations based on a defined acceptability criterion for the system, wherein the defined acceptability criterion corresponds to an acceptable operational performance metric for the system. In some implementations, the acceptability criterion can be received from a device administrator. With these implementations, the computer executable components can include an acceptability criteria component that facilitates receiving manual input selecting or defining the defined acceptability criterion. In other implementations, the acceptability criteria component can employ machine learning analysis of the historical operational data for the system to determine the defined acceptability criterion.

In some implementations, the extraction component can employ structured or semi-structured domain knowledge to determine the structured candidate interpretations. In accordance with these implementations, the computer executable components can further comprise a rule generator component that converts the structured candidate interpretations into respective computer readable algorithms using the structured or semi-structure domain knowledge. The validation component can further determine the measures of validity of the structured candidate interpretations based on evaluation of the historical operational data using the respective computer readable algorithms.

In other implementations, the computer executable components can further comprise a feedback component that receives feedback that can be used to control or streamline one or more operations of extraction component, the validation component, the rule generator component and other potential components of the device. For example, in one implementation, the feedback component can receive information regarding a desired output of the structured candidate interpretations. In accordance with this example, the computer executable components can further comprise a filtering component that filters the structured candidate policy interpretations based on feedback.

In one or more additional embodiments, the device can further comprise a structuring component that generates a computer readable formalized representation of the one or more structured candidate policy interpretations. In accordance with these embodiments, the computer executable components can further comprise a compliance evaluation component that evaluates compliance with the rule based on the computer readable formalized representation. For example, in one implementation, the system comprises an insurance organization and the unstructured information defines an insurance claim policy of the insurance organization. In accordance with this implementation, the compliance evaluation component can evaluate received insurance claims using the computer readable formalized representation of the structured candidate policy interpretations to determine whether the received insurance claims violate the insurance claim policy.

In some embodiments, elements described in connection with the disclosed systems can be embodied in different forms such as a computer-implemented method, a computer program product, or another form.

DETAILED DESCRIPTION

Figure 1:
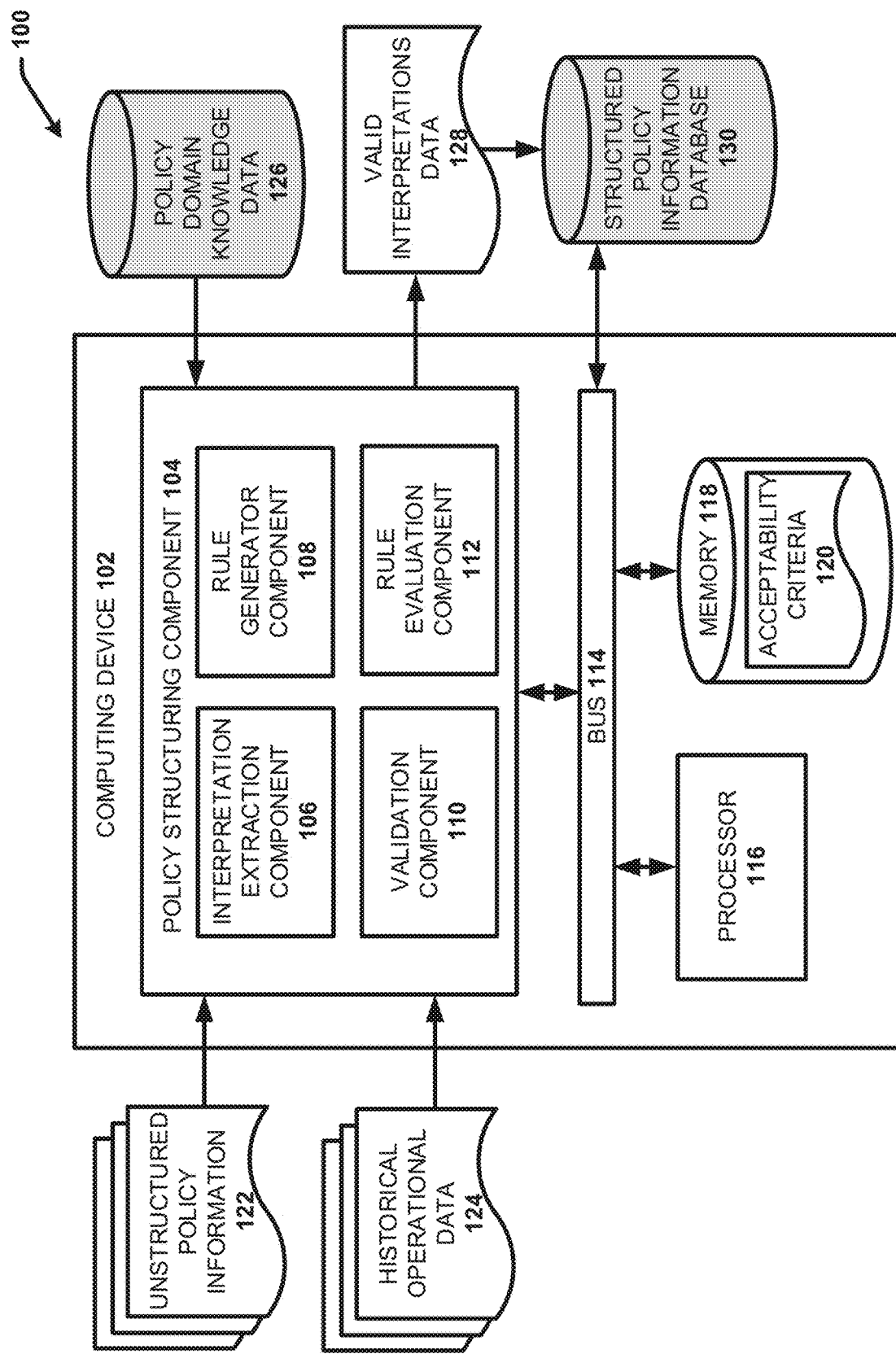
FIG. 1 illustrates a block diagram of an example, non-limiting system that facilitates extracting structured policy rules from unstructured policy documents in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Summary section or in the Detailed Description section.

The subject disclosure provides systems, computer-implemented methods, apparatus and/or computer program products for extracting structured policy rules, such as business policy rules, from unstructured policy documents, such as an electronic format of a manual or book defining operational policies of a business. Business policies are the guidelines developed by an organization to govern its actions. They define the limits within which decisions must be made. Business policies can also define rules and requirements associated with acquisition of resources with which organizational goals can be achieved. For example, many business organizations define operational policies that provide rules and requirements regarding financial affairs, roles and responsibilities, quantitative and qualitative performance standards, handling business assets, and the like. Business policies are carefully developed and implemented to facilitate achieving optimal performance of a business's goals. However, business policy guidelines are generally described in multiple, unstructured policy documents and semi-structured tables containing codes and industry specific or domain specific dictionaries and coding systems. Accordingly, ensuring effective application and compliance with business policy guidelines often requires careful manual review and understanding of large volumes of diverse data by individuals that are experts in the field.

The disclosed subject matter provides computer-implemented techniques for automatically extracting business rules and requirements from unstructured, (electronic) policy documents, and converting them into a formalized or structured computer readable format, such as a structured computer readable algorithm. The formalized computer readable form of the business rule can further be used by a computing system to automatically ensure or facilitate compliance with the business rules and requirements in association with continued operations of the business. For example, as applied to an insurance company, an insurance policy provided by the insurance company can define rules and requirements regarding what types of claims can be submitted by what entities, content of the claims, restrictions for fulfilling the claims, and the like. The various rules and requirements of an insurance policy are generally defined in several unstructured documents including text, tables, definitions, and the like. In accordance with this example, the disclosed computer implemented techniques can employ one or more computer executable components that identify and extract defined policy rules included in the unstructured insurance policy documents and convert the defined policy rules into computer readable formalized representations of the policy rules. For instance, assuming a medical insurance policy has a rule that restricts claims for reimbursement for procedure X to be submitted with pre-authorization form Y. The disclosed techniques provide for identifying and extracting this rule from an unstructured insurance policy document and converting the rule into a formalized, computer readable format. The formalized policy rules can be used in various capacities, such as employing them to automatically evaluate compliance of newly submitted claims with the policy, used to generate additional policy rules, used to identify and prioritize policy rules based on relative importance to one or more target goals of the policy or otherwise used to optimize policy rules in association with achieving a defined goal, used to identify discrepancies between policy rules, and the like. As a result, manual review of the various unstructured policy documents to identify and clearly understand the rules of the policy in association with applying the policy to newly received claims can be replaced or supplemented by an automated mechanism for performing the same task in a much more efficient, consistent and accurate manner.

In one or more embodiments, the disclosed techniques for automatically extracting policy rules and requirements from unstructured policy documents and converting them into a formalized computer readable format can initially involve identifying an unstructured representation of a policy rule or requirement included in an unstructured policy document and generating one or more candidate interpretations of the policy rule or requirement. In various implementations, the one or more candidate interpretations of the policy rule or requirement can be generated and/or extracted from the unstructured policy document in accordance with a structured, computer readable format. For example, in some embodiments, natural language processing (NPL) can be used to parse through unstructured policy text to identify a potential policy rule or requirement and to extract or generate one or more different structured interpretations of the policy rule or requirement. Additional structured or semi-structured information (in addition to the unstructured policy documents) associated with the particular domain for which the policy is defined (e.g., particular business domain, an particular enterprise, a particular type of system, etc.), can be also be used to facilitate identifying, extracting and/or generating the structured representations of the candidate interpretations of the policy rule/requirement. For example, such additional structured or semi-structured information can include defined ontologies, rule schemas, business rules, domain knowledge and the like. In some implementations, the respective structured interpretations of the policy rule or requirement can further be converted into a structured rule or algorithm format of the policy rule or requirement based on the guidance provided by structured or semi-structured domain specific ontologies, schemas and the like.

The different interpretations of a policy rule or requirement can further be vetted for validity to determine which interpretation of the policy rule/requirement is correct. In some implementations in which a policy rule can be broken down into two or more requirements, (e.g., minimum age is X; maximum age is Y), two or more interpretations of the policy can be determined to be correct. In various embodiments, the different interpretations can be vetted for validity using historical operational data reflective of performance of operations of the business, enterprise, system, etc., for which the policy is defined, to determine whether and/or to what degree the respective interpretations accurately reflect the standard operations of the business, enterprise, system, etc. For example, using the medical insurance claim policy example above, assume a potential interpretation of a policy rule is characterized as follows: reimbursement for procedure X is only authorized if submitted with pre-authorization form Y. In accordance with this example, the historical claims data can be evaluated to determine that 95% of claims submitted for procedure Y that were authorized were in fact submitted with pre-authorization form Y. Accordingly, given the high percentage of claims that match the policy rule interpretation, the system can consider the particular policy interpretation as valid.

In some embodiments, one or more acceptance criteria can be defined that can be used to facilitate determining whether a particular interpretation of a policy rule is valid based on the results of the evaluation of the interpretation of the policy rule using the historical operational data. In this regard, the results can be evaluated based on some given business acceptability criteria that reflects a defined notion of normal behavior/output for the business industry in order to select the optimal interpretation of the unstructured source data among the different extracted interpretations. For example, in accordance with the insurance claim example above, an acceptability criterion could require a particular interpretation of a policy rule to be characterized as an invalid or incorrect interpretation if it invalidates 60% of the claims. In this regard, because the particular example interpretation of the policy rule only invalidates 5% of the claims, this example interpretation of the insurance policy claim rule can be considered a valid and accurate interpretation.

Various embodiments of the disclosed techniques are exemplified in association with evaluating insurance policies, and more particularly to healthcare insurance claim policies, based on historical claims data, wherein providers (e.g., doctors, hospitals, etc.) submit claims to a payer (e.g., a health insurance agency) for services rendered to patient. For example, the historical claims data can reflect whether the payer paid a claim (rendering the claim valid) or rejected the claim (rendering the claim invalid), based on the eligibility criteria for a particular service which are determined by the insurance policy guidelines. In accordance with these embodiments, the eligibility criteria described in a healthcare insurance policy can be modeled as business rules that describe various restrictions and requirements for authorizing claims, such as but not limited to: eligible providers (e.g., required role/license, physicians, nurses, etc.), eligible places of service (e.g., at home, in a hospital), maximum units of service, durable equipment that a provider should report for a single patient in a given period, groups of services that should not be reported together (in combination) for the same patient in a single date, services that are inappropriate for a particular type of patient, and so on.

However, the disclosed techniques can be applied to various domains and are not limited to evaluating and processing insurance policies. In this regard, the disclosed techniques can be applied to evaluate policy documents for various types of enterprises, systems, and the like, for which historical operational information is available that reflects performance of operations of the enterprise or system in accordance with the policy rules and requirements defined for the enterprise or system. For example, the disclosed techniques can be employed in legal domains to automatically extract structured rules from unstructured legal policy documents based on evidence documenting outcomes of application of the legal policies to real-word scenarios. In another example, the disclosed techniques can be used in the healthcare industry to facilitate automated understanding and extraction of healthcare policies defining clinical workflows for different patients, diagnosis, institutions and the like, based on historical workflow information reflecting clinical practice in accordance with the healthcare policies. In another example, the disclosed techniques can be applied to a transportation system, such as an airline industry, for which operational policies are defined that provide rules, requirements, protocols, etc., regarding operating aircrafts, following a schedule, responding to delay codes, interacting with passengers, etc. According to this example, the disclosed techniques can be employed to extract many complex operational policy rules from various internal guideline documents for a particular airline enterprise, regulatory agency documents that govern all aircraft policies for different airports and airspaces, and the like, based on historical operational data for the particular airline enterprise and other airline enterprises.

Accordingly, although various embodiments are exemplified in association with evaluating a policy for a business, it should be appreciated that the disclosed techniques are not limited to policies for an organization or economic system where goods and services are exchanged for one another or for money. In this regard, the disclosed techniques can be applied to policies for various types of businesses, enterprises, organizations, systems, institutions, and the like. In various embodiments, the terms business, enterprise, organization, system, institution and the like, are used interchangeably. The term "policy" as used herein can refer to a deliberate system of principles to guide decisions and achieve rational outcomes adopted or proposed by a business, enterprise, organization, system, individual, and the like. In this regard, a policy can include but is not limited to, rules, requirements, laws, regulations, guidelines, directions, etc. that are designed to control or influence one or more operations of a business, enterprise, organization, system, etc., for which the policy is defined.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting system 100 that facilitates extracting structured policy rules from unstructured policy documents in accordance with one or more embodiments of the disclosed subject matter. System 100 and other systems detailed herein can provide substantial technical improvements in association with automated information extraction from unstructured or semi-structured electronic documents. System 100 provides a new approach for automated information extraction by extracting interpretations of business (or enterprise, system, etc.) policies from unstructured policy documents to generate or facilitate generating structured algorithms or rules corresponding to the respective interpretations. The structured algorithms or rules can further be validated using historical operational data reflective of actual business operations that the policies are designed to govern/guide to select the optimal interpretations that harmonize with the historical operational data. In this regard, unlike traditional information extraction approaches that extract structured information from unstructured sources and perform disambiguation based on an ontological context or domain model, system 100 examines potential interpretations of extracted business policy rules/requirements in the context of an operational problem that the rule or requirement is intended to solve. As a result, the information extraction techniques provided by system 100 are not susceptible to potential extraction of policy rules that are in theory consistent with a defined business model or ontology, yet very unlikely when applied to an actual business scenario, and thus not accurate reflections of actual business policy rules/requirements defined by the policy.

System 100 and/or the components of system 100 (and other systems disclosed herein) can be employed to use hardware and/or software to solve problems that are highly technical in nature, that are not abstract, and that cannot be performed as a set of mental acts by a human. System 100 and/or components of system 100 or other systems described herein can also be employed to solve new problems that arise through advancements in technology, computer networks, the Internet, and the like. The techniques provided by system 100 for automatically extracting the knowledge required to solve a business problem is a strong market differentiator in many scenarios, such as finance and healthcare. For example, with respect to the healthcare reimbursement industry, medical insurance policies are often described in multiple, unstructured policy documents and semi-structured tables containing medical procedure codes and healthcare agency regulations, medical terminology and the like. Accordingly, ensuring effective application and compliance with medical insurance policies often requires careful manual review and understanding of large volumes of diverse data by individuals that are experts in the field. For example, policy investigators are often required to manually research data and policies to support improper payment investigation. This is an extremely time-consuming process for investigators and results in poor policy coverage. System 100 however provides for automatically extracting structured data and business rules from unstructured policy documents, such as medical insurance policies, to provide automatic or semi-automatic claim auditing support to automatically identify submitted and/or fulfilled claims that do not comply with policy requirements. In this regard, the information extraction techniques provided by system 100 can be used to automatically identify and/or facilitate policy/regulation analysts to identify policy violations by deriving knowledge from unstructured and semi-structured documents, such as insurance claim policies and regulations. System 100 can further interpret this knowledge to assist in the building of structured algorithms and business rules that can be used to ensure compliance faster, more accurately and for more impactful topics.

Embodiments of systems described herein can include one or more machine-executable components embodied within one or more machines (e.g., embodied in one or more computer readable storage media associated with one or more machines). Such components, when executed by the one or more machines (e.g., processors, computers, computing devices, virtual machines, etc.) can cause the one or more machines to perform the operations described. For example, in the embodiment shown, system 100 includes a computing device 102 that includes a policy structuring component 104. The policy structuring component 104 further includes an interpretation extraction component 106, a rule generator component 108, a validation component 110, and a rule evaluation component 112. In this regard, the policy structuring component 104, the interpretation extraction component 106, the rule generator component 108, the validation component 110, and the rule evaluation component 112 can respectively correspond to machine-executable components. System 100 also includes various electronic data sources and data structures comprising information that can be read by, used by and/or generated by policy structuring component 104. For example, these data sources and data structures can include but are not limited to: unstructured policy information 122, historical operational data 124, policy domain knowledge data 126 data, valid interpretations data 128 and structured policy information database 130.

The computing device 102 can further include or be operatively coupled to at least one memory 118 and at least one processor 116. In various embodiments, the at least one memory 118 can store executable instructions (e.g., the policy structuring component 104, the interpretation extraction component 106, the rule generator component 108, the validation component 110, and the rule evaluation component 112) that when executed by the at least one processor 116, facilitate performance of operations defined by the executable instruction. In the embodiment shown, the memory 118 can further store the acceptability criteria 120 information that can be used by the rule evaluation component 112 to facilitate selecting valid interpretations of rules and requirements included in the unstructured policy information 122 evaluated by system 100. In some embodiments, the memory 118 can also store the various data sources and/or structures of system 100 (e.g., the unstructured policy information 122, the historical operational data 124, the policy domain knowledge data 126, the valid interpretations data 128 and/or the and structured policy information database 130). In other embodiments, the various data sources and structures of system 100 can be stored in other memory one or more remote device or systems that are accessible to the computing device 102 (e.g., via one or more networks). The computing device 102 can further include a device bus 114 that communicatively couples the various components and data sources of the computing device 102. Examples of said processor 116 and memory 118, as well as other suitable computer or computing-based elements, can be found with reference to FIG. 10, and can be used in connection with implementing one or more of the systems or components shown and described in connection with FIG. 1 or other figures disclosed herein.

In some implementations, the computing device 102, and/or the various components and data sources of system 100 can be communicatively connected via one or more networks. Such networks can include wired and wireless networks, including but not limited to, a cellular network, a wide area network (WAD, e.g., the Internet) or a local area network (LAN). For example, the computing device 102 can communicate with one or more external devices providing the unstructured policy information 122, the historical operational data 124, and/or the policy domain knowledge, the structured policy information database 130 (and vice versa), using virtually any desired wired or wireless technology, including but not limited to: wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Zigbee and other 802.XX wireless technologies and/or legacy telecommunication technologies, BLUETOOTH®, Session Initiation Protocol (SIP), ZIGBEE®, RF4CE protocol, WirelessHART protocol, 6LoWPAN (IPv6 over Low power Wireless Area Networks), Z-Wave, an ANT, an ultra-wideband (UWB) standard protocol, and/or other proprietary and non-proprietary communication protocols. The computing device 102 can thus include hardware (e.g., a central processing unit (CPU), a transceiver, a decoder), software (e.g., a set of threads, a set of processes, software in execution) or a combination of hardware and software that facilitates communicating information between the computing device 102 and externals systems, sources and devices.

The policy structuring component 104 can facilitate various operations associated with interpreting a policy for a business, enterprise, system, organization and the like, defined in one or more unstructured policy documents, represented in system 100 as unstructured policy information 122, and automatically extracting and/or generating structured representations of rules, requirements, protocols, laws, etc. (collectively and generally referred to herein as rules), included in the unstructured policy information 122. In this regard, the policy structuring component 104 can facilitate extracting and transforming the unstructured rules and requirements into a structured format that corresponds to a formalized or standardized computer readable format that can be used to perform various actions associated with evaluating the policy, facilitating compliance with the policy and the like. In the embodiment shown, the policy structuring component 104 can include interpretation extraction component 106, rule generator component 108, validation component 110 and rule evaluation component 112.

In one or more embodiments, the interpretation extraction component 106 can parse through or otherwise evaluate the unstructured policy information 122 to identify potential policy rules and requirements represented in the unstructured policy information 122. The interpretation extraction component 106 can further extract and/or generate one or more structured interpretations of an identified policy rule or requirement included in the unstructured policy information 122. For example, the interpretation extraction component 106 can parse through sentences, phrases and the like describing rules of a business policy and extract or generate a streamlined, structured version of a potential policy rule. In various implementations, the interpretation extraction component 106 can extract and/or generate a plurality of different candidate interpretations of a policy rule or requirement included in the unstructured policy information 122. The extracted and/or generated structured interpretations of the identified policy rules and requirements can be formatted and/or stored in accordance with a defined data model or structured format. In some implementations, the structured interpretations can be stored in or otherwise associated with a knowledge graph.

The unstructured policy information 122 can include one or more electronic documents or files including unstructured information defining various rules, requirements, protocols, definitions, etc. of a policy. For example, the unstructured policy information 122 can include an electronic format of a manual or book defining operational policies of a business in multiple, unstructured policy documents and semi-structured tables containing codes and industry specific or domain specific dictionaries and coding systems. In another example, the unstructured policy information 122 can also include a written contract, volumes of a legal policy or manual, a guidebook, an instruction chart, a pamphlet, and the like. The unstructured policy information 122 can thus include several pages of text, definitions, tables, indexes, reference pages, hyperlinks, and the like. The type of unstructured information included in the unstructured policy information 122 will vary depending on the type of policy with which it is associated. For example, in implementations in which the policy is a health insurance policy, the unstructured policy information 122 can define rules and regulations regarding what types of claims can be submitted, entities that can submit the claims, requirements of the claims, restrictions on claims and the like.

Unstructured information or data generally refers to information that either does not have a pre-defined data model or is not organized in a pre-defined manner. In accordance with the context of the disclosed subject matter, the term unstructured information or unstructured data is used to refer to information or data in a format that is not (or otherwise does not follows) a formalized or defined computer readable format or data model used by the policy structuring component 104 (or another system affiliated with system 100). For example, the unstructured policy information 122 can include text written in natural language, information included in the form of a table or chart, and the like. In some implementations, in addition to text the unstructured policy information 122 can include symbols, numbers, icons, images, and the like audio files, video files, and other forms of mixed media or multimedia files.

The techniques employed by the interpretation extraction component 106 to identify, extract and/or generate the one or more structured interpretations of rules or requirements included in the unstructured policy information 122 can vary. For example, the interpretation extraction component 106 can employ one or more techniques, including but not limited to: natural language processing (NPL), deep NPL parsing (e.g., using one or more neural networks), portable document format (PDF) parsing, text passage classifiers, entity extraction, (un)supervised frequent pattern learning, and semantic filtering, among others. In some embodiments, the interpretation extraction component 106 can be configured to employ different information extraction techniques or different combinations of information techniques to generate different candidate interpretations of a potential rule or requirement included in the unstructured policy information 122. In this regard, the different interpretations can reflect usage of different extraction techniques or different extraction technique combinations, which can have varying strengths and weaknesses depending on the type of unstructured data being evaluated. By using different information extraction techniques to generate different candidate interpretation of a potential policy rule or requirement, system 100 can capitalize on the strengths and weakness of the different techniques to ensure that at least one of the interpretations represents of a policy rule or requirement corresponds to the most optimal interpretation possible, removing potential bias that could be introduced by using a single information extraction technique to generate the different candidate interpretations.

In some embodiments, the interpretation extraction component 106 can employ policy domain knowledge data 126 (if available) to facilitate identifying, extracting, and/or generating one or more structured representations of a policy rule or requirement included in the unstructured policy information 122. For example, the policy domain knowledge data 126 can include additional (in addition to the unstructured policy documents) structured or semi-structured information associated with the domain (e.g., the particular business, enterprise, system, etc.) of the policy represented by the unstructured policy information 122. For instance, the policy domain knowledge data 126 can include but is not limited to: ontology information providing defined ontologies used in the domain, knowledge graph information defining one or more knowledge graphs used in the domain, dictionary or term information defining terms and associated definitions used in the domain, taxonomies, data models defining relationships between data objects associated with the domain, tables, business rules schemas, and the like. For example, with respect to the healthcare industry, the policy domain knowledge data 126 can include information defining procedure codes, medical terms, information relating data objects associated with specific medical services to one another, and the like.

The rule generator component 108 can convert the one or more structured interpretations of a policy rule or requirement extracted and/or generated by the interpretation extraction component 106 into a structured rule or algorithm format. For example, in some implementations, the interpretation extraction component 106 can extract and/or generate a first structured representation of an unstructured policy rule or requirement, and the rule generator component 108 can further streamline the first structured representation to generate a second structured representation of the policy rule or requirement that corresponds to a computer readable algorithm or rule. In various embodiments, the rule generator component 108 can generate a computer readable algorithm form of a policy rule or requirement based on the guidance provided by the policy domain knowledge data 126 data (if available). For example, the rule generator component 108 can ingest and lift structured or semi-structured data associated with a policy (e.g., tables, sheet, dictionaries) and other domain knowledge (e.g., defined ontologies, rule schemas, etc.) included in the policy domain knowledge data 126 to generate a connected knowledge graph in order to discover and infer meaningful semantic patterns among the data. The rule generator component 108 can further employ the semantic patterns and the initial extracted and/or generated structured interpretations of the policy rules or requirements to convert the interpretations into structured, computer readable algorithms that can applied to the historical operational data 124. In this regard, the rule generator component 108 can use the ingested domain knowledge to infer the semantic patterns that are needed in order to transform the policy interpretations from the previous component into a computable-executable format, such as rules or queries. For example, in one implementation, the rule generator component 108 can convert an extracted interpretation of a policy rule or requirement in a first structured format into a structured, computer readable algorithm format, or formal query format, such as a structured query language (SQL) file format, or a similar format.

The validation component 110 can evaluate the validity of different interpretations of a policy rule, requirement, protocol, etc., using historical operational data 124 reflective of historical performance of operations of the business, enterprise, system, etc., for which the policy is defined, to determine whether and/or to what degree the respective interpretations accurately reflect the operations of the business, enterprise, system, etc. For example, the historical operational data 124 can include information that reflects operations performed or conducted by the business, enterprise, system, organization, etc., under a policy (represented by the unstructured policy information 122), that provides rules, requirements, protocols and the like, intended to control the operations. For example, in implementations in which the policy being evaluated is an insurance policy, the historical operational data 124 can include claims data identifying submitted claims, details regarding the submitted claims, information regarding whether the claims were accepted or rejected, information indicating why a claim was rejected, information indicating an amount of reimbursement provided for accepted claims, and the like. In this regard, the historical operational data 124 can reflect performance of operations of the business, enterprise, system, etc., according to the rules and requirements of the policy. Accordingly, the validation component 110 can evaluate structured interpretations of policy rules and requirements generated by the interpretation extraction component 106 and/or the rule generator component 108 to determine information regarding whether and to what degree the structured rules or requirements are reflected in the historical operational data 124, and thus serve a valid, practical and/or intended purpose of the business.

For example, in one or more embodiments, the validation component 110 can apply a structured algorithm or rule format of a policy rule interpretation (e.g., determined by the rule generator component 108) to the historical operational data 124 to generate output information that indicates whether and/or to what degree the policy rule interpretation reflects a business solution observed in the historical operational data 124. The output results determined by the validation component 110 can vary based on the different interpretations of a policy rule or requirement. For example, assume an insurance claim rule is associated with two candidate interpretations, wherein a first interpretation defines the rule as 'all claims for procedure Y must be submitted with pre-authorization form X,' and a second interpretation defines the rule as 'claims for procedure Y must be submitted with pre-authorization form X if received for patients with condition C.' According to this example, only one of these interpretations can be correct. To facilitate determining which interpretation is correct, the validation component 110 can use the historical operational data 124, such as historical claims data, to determine whether the historical operational data supports the first interpretation or the second interpretation. For instance, the validation component 110 can determine a percentage of claims which support the first interpretation and a percentage of claims which support the second interpretation. In this regard, the interpretation associated with the higher percentage could be considered the correct interpretation.

It should be appreciated that although policy guidelines may be defined for a business, enterprise, system, etc., depending on the nature of the business, in practice, scenarios may be observed wherein the operation performed did not follow or conform to the rules and regulations defined by the business policy. As a result, the historical operational data 124 may include information that reflects performance of operations against policy. In some embodiments, information included in the historical operational data 124 that reflects behavior that goes against policy can be identified and evaluated by the policy structuring component 104 in association with the evaluation process. In this regard, the policy structuring component can uncover regularly abused or violated policy rules included reflected by the historical operational data 124 and flag these policy rules for additional review (e.g., to notify a policy enforcing entity, to refine the policy rules to minimize abuse, etc.). In other embodiments, the historical operational data 124 can be preprocessed and cleansed to remove this type of outlier data to facilitate ensuring the accuracy of the evaluations performed by the rule evaluation component 112.

In various embodiments, the rule evaluation component 112 can evaluate the output results of the validation component 110 to determine whether (if any) of the candidate interpretations of a policy rule or requirement are supported by the historical operational data 124 and thus characterized as a correct interpretation of the policy rule or requirement. For example, in furtherance to the example above involving two interpretations of a claim policy and wherein the validation component 110 can determine percentages of claims respectively supporting each interpretation, the rule evaluation component 112 can be configured evaluate the percentage information to determine which interpretation is correct. In the example above, the interpretation associated with the higher percentage is suggested as being the correct interpretation of the two. However, as discussed in greater detail below, the criteria and/or mechanism employed by the rule evaluation component 112 to determine whether a candidate interpretation of a policy rule can be considered valid can vary. In some implementations in which a policy rule can be broken down into two or more requirements, (e.g., minimum age is X; maximum age is Y), two or more interpretations of the policy can be determined to be correct. With these implementations, an optimal interpretation of a policy rule or requirement can include a combination of different candidate interpretations. The rule evaluation component 112 can further select the interpretations that are considered correct or valid interpretations and generate output information including the selected valid interpretations, represented in system 100 as valid interpretations data 128. Accordingly, the rule evaluation component 112 can filter out potentially incorrect interpretations of the unstructured policy information 122 to generate a vetted, valid set of structured policy rules and requirements based on the unstructured policy information 122.

In one or more embodiments, the rule evaluation component 112 can determine or infer whether an interpretation of a policy rule/requirement is valid using (predefined) acceptability criteria 120. The acceptability criteria 120 can reflect a defined notion of normal behavior/output for the business industry for which a policy is defined. For example, the acceptability criteria 120 can include quantitative and/or qualitative metrics for evaluating the results of the validation component 110 to determine whether a particular interpretation is valid or invalid. The types of metrics can vary based on the policy being evaluated, the type of rule being evaluated, and the like. For example, in some implementations in which the policy is an insurance policy, the acceptability criteria can include a metric that characterizes interpretations which reflect more than X percent of the historical claims as valid. In another example, the acceptability criteria 120 can specify the number of illegitimate claims should be less than 10%. Based on the historical data as applied to a particular interpretation of an insurance policy, the validation component 110 can determine that approximately 7.3% of the claims are illegitimate based on the interpretation. Thus, the rule evaluation component 112 can determine that the interpretation is valid. In some implementations, the acceptability criteria 120 can provide thresholds for valid verses invalid interpretations. For example, if a rule interpretation flags a high percentage (e.g., relative to a defined threshold) of claims as illegitimate, then the rule evaluation component 112 can automatically determine that interpretation is inaccurate and thus reject the interpretation. As described infra, in some embodiments, the acceptability criteria 120 can be manually specified (e.g., by domain experts, by policy generators, etc.). In other embodiments, the acceptability criteria 120 can be inferred or learned using one or more machine learning techniques.

The valid interpretations data 128 can include one or more structured forms of a selected, valid policy interpretation (or combination of valid policy interpretations). For example, in some implementations, the valid interpretations data 128 can include a structured or formalized format of a policy rule extracted and/or generated by the interpretation extraction component 106. The valid interpretations data 128 can also include a structured algorithm form of the policy rule generated by the rule generator component 108. In some implementations, the results of the validation component 110 can also be included with the valid interpretations data 128 (e.g., information indicating a valid claim interpretation was supported by X percent of the historical claims data, and the like). In various embodiments, the selected, valid interpretations for a policy included in the valid interpretations data 128 can be collated, indexed, and otherwise organized into a formalized computer readable data structure that can be stored in a structured policy information database 130. For example, one suitable data structure can include a knowledge graph consisting of relevant facts and business rules extracted from the unstructured policy information 122. The collated and indexed structured policy representations include in the structured policy information database 130 can be used for various purposes. For example, as discussed in greater detail infra, structured forms of policy rules and requirements included in the structured policy information database 130 can be used to facilitate, regulate and/or ensure policy compliance, in automated manner with increased efficiency and accuracy while focusing on more the most impactful topics.

Figure 2:
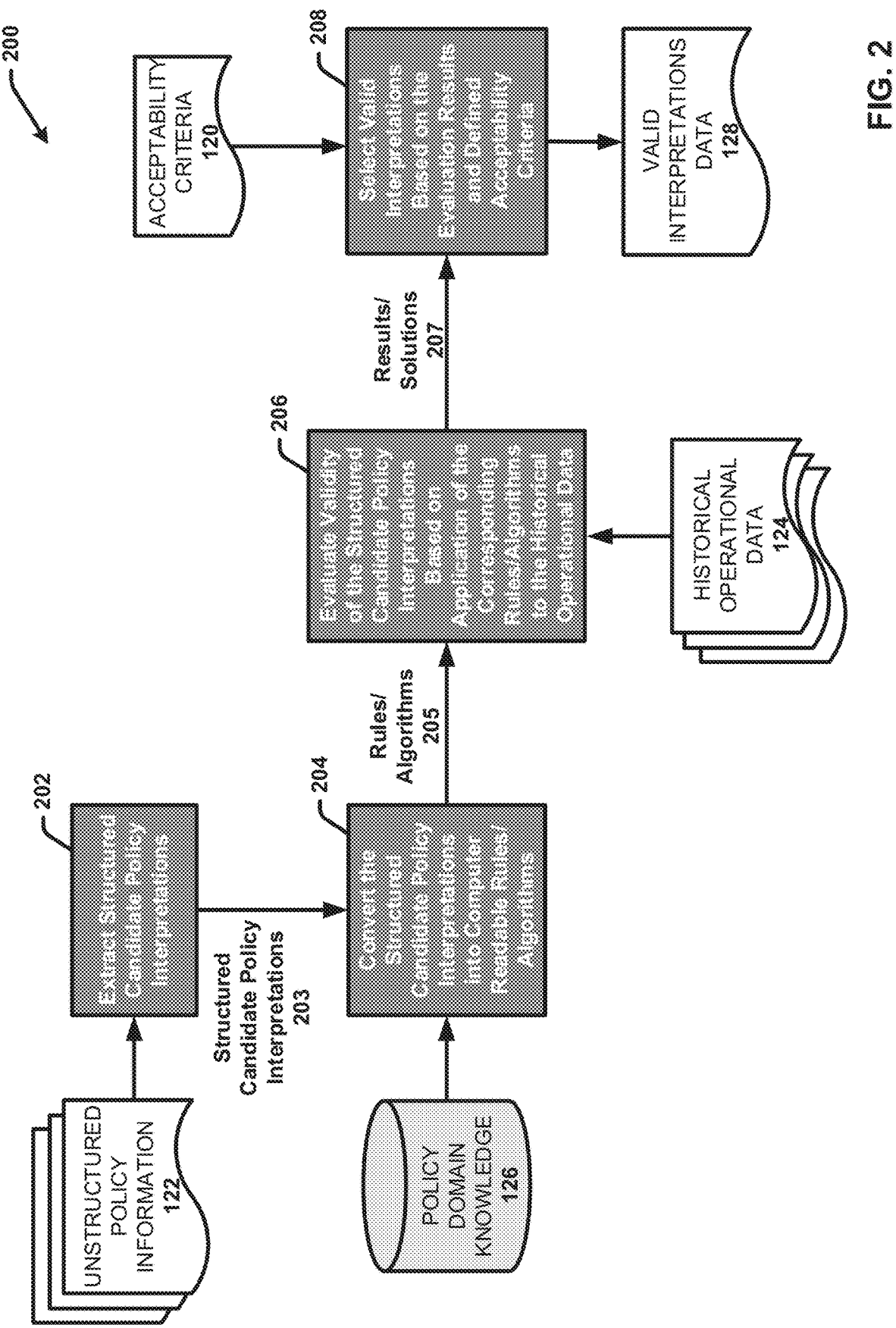
FIG. 2 provides a high-level flow diagram of an example computer-implemented process for extracting structured policy rules from unstructured policy documents in accordance with one or more embodiments of the disclosed subject matter.

FIG. 2 provides a high-level flow diagram of an example computer-implemented process 200 for extracting structured policy rules from unstructured policy documents in accordance with one or more embodiments of the disclosed subject matter. In this regard, process 200 demonstrates an example process that can be implemented by system 100 (e.g., using the interpretation extraction component 106, the rule generator component 108, the validation component 110 and the rule evaluation component 112) in accordance with one or more embodiments. Process 200 can be applied to generate vetted and valid, structured representations of unstructured rules and requirements for various types of policies associated with various types of domains. Repetitive description of like elements employed in respective embodiments is omitted for sake of brevity.

With reference to FIGS. 1 and 2, at 202, structured candidate policy interpretations 203 can be extracted from unstructured policy information 122 (e.g., via the interpretation extraction component 106). At 204, the structured candidate policy interpretations 203 can be converted into computer readable rules/algorithms 205 corresponding to the respective structured candidate representations (e.g., via the rule generator component 206). In the embodiment shown, policy domain knowledge data 126 (e.g., ontologies, business rules schema, etc.) can be used to facilitate understanding and structuring an interpretation of unstructured policy rule into a structured computer readable algorithm representation of the interpretation. At 206, the validity of the structured candidate policy interpretations can be evaluated based on application of the corresponding computer readable rules/algorithms 205 to the historical operational data 124 (e.g., via the validation component 110) to generate results/solutions 207. The results/solutions can include information that indicates whether and/or to what degree an interpretation of a policy rule is supported by the historical operational data 124. For example, the historical operational data 124 can be queried using the corresponding rules/algorithms to determine measurable values indicative of an amount of the operational data that matches or satisfies a representative policy rule algorithm. In some implementation, the operational data that matches or satisfies the representative policy rule can be extracted to determine relevant parameters associated with the operational data.

At 208, the results/solutions 207 of the historical operational data evaluation can be used, along with the acceptability criteria 120, to select one or more valid interpretations (if any) from among the structured candidate policy interpretations. In this regard, the final output of process 200 includes valid interpretations data 128, which can include the selected valid interpretations from among the structured candidate policy interpretations. For example, for each (or in some implementations one or more) selected valid interpretation, the valid interpretations data 128 can include the structured form of the policy interpretation generated at 202, and/or the computer readable algorithm or rule form of the interpretation generated at 204. In some implementations, the associated results/solutions determined for a particular valid interpretation can also be included in the valid interpretations data 128. Still in other embodiments, the valid interpretations data 128 can be re-formatted and/or organized into another defined format, such as a knowledge graph (e.g., by the policy structuring component 104).

Figure 3:
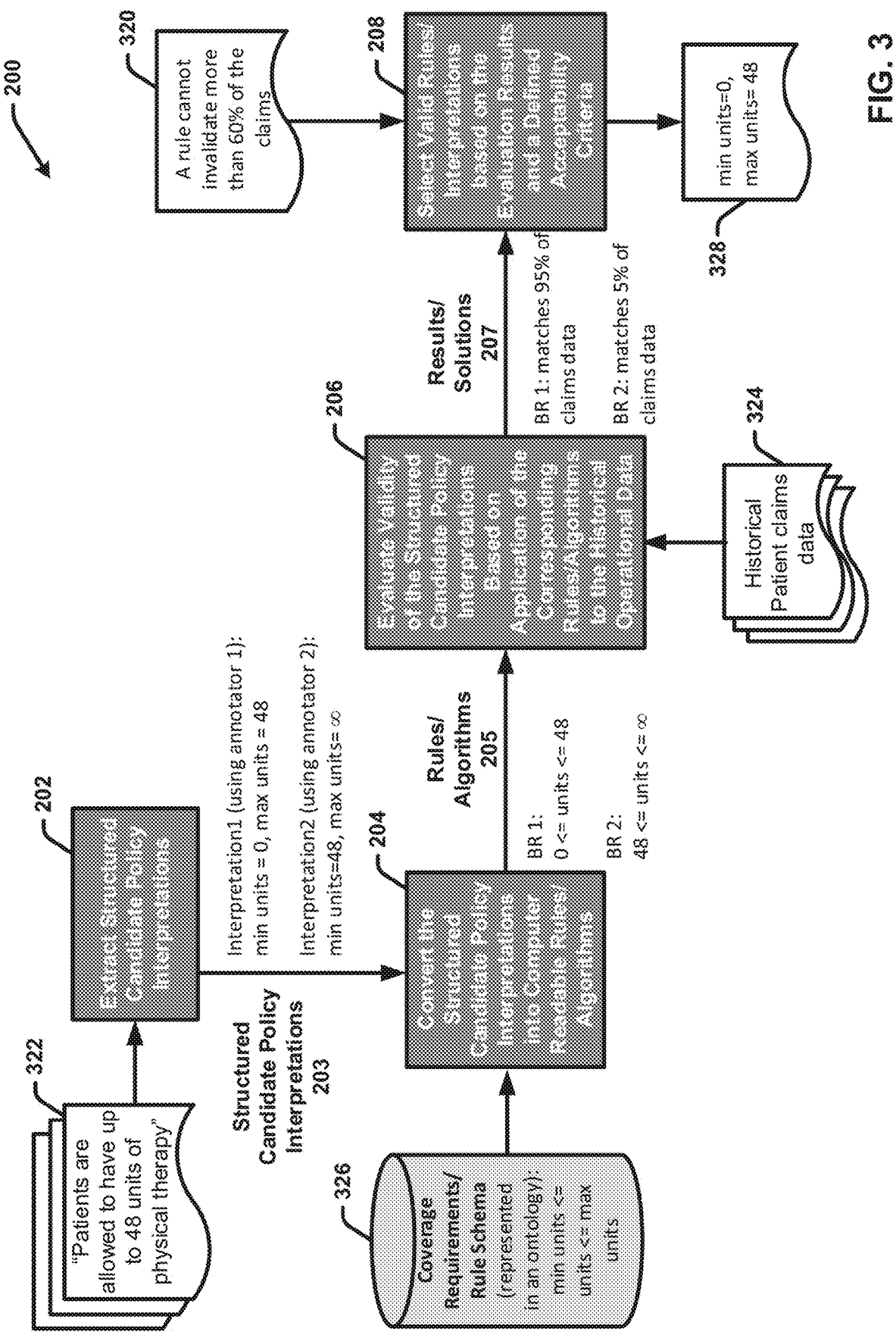
FIG. 3 provides a high-level flow diagram of an example computer-implemented process for extracting structured insurance policy rules from unstructured insurance claim policy documents in accordance with one or more embodiments of the disclosed subject matter.

FIG. 3 provides another high-level flow diagram of example computer-implemented process 200 as exemplified in association with usage of process 200 to extract structured insurance policy rules from unstructured insurance claim policy documents in accordance with one or more embodiments of the disclosed subject matter. Repetitive description of like elements employed in respective embodiments is omitted for sake of brevity.

With reference to FIGS. 1, 2 and 3, at 202, structured candidate policy interpretations 203 can be extracted from unstructured policy information 322 (e.g., via the interpretation extraction component 106). In accordance with this example implementation, the unstructured policy information can include documents of a medical insurance policy and provide various unstructured rules and requirements associated with submitting and authorizing medical claims. For instance, one example policy rule included in the unstructured policy information 322 can include the statement "patients are allowed to have up to 48 units of physical therapy." At 202, the interpretation extraction component 106 can evaluate this unstructured statement text to extract and/or generate one or more structured interpretations of the policy statement (e.g., using NPL and/or various techniques described herein). For example, in the embodiment shown, the structured candidate policy interpretations 203 include two different structured interpretations of this policy statement. For example, a first structured interpretation (interpretation 1) interprets the policy statement as defining a minimum (min) number of units equal to 0, and a maximum (max) number of units equal to 48, provided in structured notation (min units=0, max units=48). The second structured interpretation (interpretation 2) interprets the policy statement as defining a minimum number of units equal to 48, and a max number of units equal to ∞, provided in structured notation (min units=48, max units=∞).

At 204, the structured candidate policy interpretations 203 can be converted into computer readable rules/algorithms corresponding to the respective structured candidate representations (e.g., via the rule generator component 206) based on available policy domain knowledge 326. For example, in the embodiment shown, the policy domain knowledge 326 can include coverage requirements and rule schema data (e.g., represented by a defined ontology, such as min units<=units<=max units). The corresponding computer readable rules/algorithms 205 for the first and second interpretations are respectively referred to as business rule 1 (BR 1) and business rule 2 (BR 2). For example, based on the rule schema min units<=units<=max units, the generated BR 1 is structured as 0<=units<=48, and BR 2 is structured as 48<=units<=∞.

At 206, the validity of the structured candidate policy interpretations 203 can be evaluated based on application of the corresponding computer readable rules/algorithms 205 to historical operational data, which in this case comprises historical patient claims data 324 (e.g., via the validation component 110). For example, the historical patient claims data 324 can be queried using the corresponding rules/algorithms BR 1 and BR 2 to determine measurable values indicative of an amount of the operational data that matches or satisfies a representative policy rule algorithm. In accordance with this example, implementation, the results/solutions 207 of the evaluation performed at 206 indicate that BR 1 matches 95% of the claims data and BR 2 matches 5% of the claims data.

At 208, the results/solutions 207 of the historical claims data evaluation can be used, along with defined acceptability criteria 320, to select one or more valid interpretations (if any) from among the structured candidate policy interpretations 203. For example, in the embodiment shown, the defined acceptability criteria 320 states that a rule cannot invalidate more than 60% of the claims. Accordingly, BR 1 can be selected as valid and BR 2 can be rejected for being invalid (as it invalidates 95% of the claims data). The selected valid interpretations of a candidate policy rule can be output in one or more defined structured formats, such as the structured formatted used for the structured candidate policy interpretations 203, the format used for the computer readable rules/algorithms 205 representation of the interpretation, or another structured/formalized representation. For example, in this example implementation, the final valid interpretations data 328 employs the format of the initial structured candidate policy interpretation corresponding to interpretation 1, (e.g., min units=0, max units=48).

Figure 4:
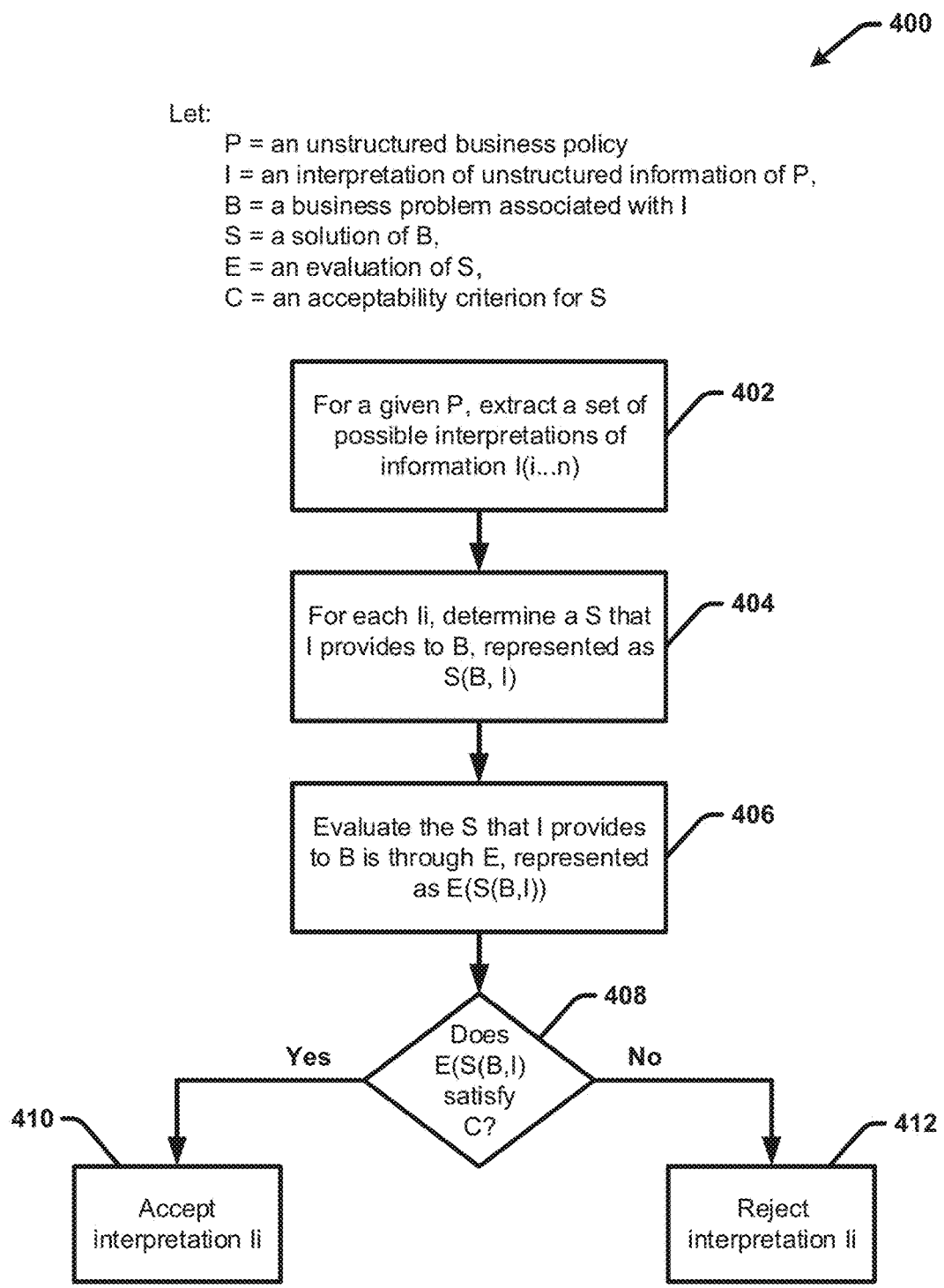
FIG. 4 provides a high-level flow diagram of an example information extraction pipeline for extracting structured policy rules from unstructured policy documents in accordance with one or more embodiments of the disclosed subject matter.

FIG. 4 provides a high-level flow diagram of an example, information extraction pipeline 400 for extracting structured policy rules from unstructured policy documents in accordance with one or more embodiments of the disclosed subject matter. Repetitive description of like elements employed in respective embodiments is omitted for sake of brevity.

System 100, process 200 and process 300 respectively describe techniques for extracting structured policy rules from unstructured policy data of a policy for a system (or business, enterprise, organization, etc.) that can be reduced at a high level to the following steps, including: extracting candidate interpretations from unstructured policy input (e.g. documents such as policies), validating the candidate interpretations in an evidence based context, wherein the evidence based context can be captured or reflected in historical operational data for the system (e.g., claims data), and/or structured or semi-structured domain knowledge (e.g., business rules schemas, ontologies, and the like used to generate corresponding algorithms for the candidate interpretations), and selecting the optimal interpretation(s) based on a defined notion of normal behavior/output for the system (e.g., the acceptability criteria).

In various embodiments, the system for which the policy is based can include a business and the policy can correspond to a business policy for the system. In accordance these embodiments, an algorithm form of a candidate interpretation of a business policy rule can be considered to represent a problem-solution function (e.g., if x then y, wherein x is the business problem and y is the solution). In this regard, evaluation of the different candidate interpretations of a policy rule using the historical operational data can correlated to a process for identifying different potential solutions to a business problem. The solutions can be evaluated to determine whether they accurately reflect a solution that is consistent with the normal operations of the business. If so, the policy interpretation can be considered valid. If not, the policy interpretation can be considered invalid.

With this concept in mind, at a high level, the disclosed techniques for extracting structured interpretations of policy rules from unstructured policy documents can be modeled as an information extraction pipeline, wherein the results are validated through the impact on a subsequent domain problem to be addressed through the extracted information. The information extraction pipeline 400 provides an example embodiment of the information extraction pipeline model for the disclosed information extraction techniques. In accordance with information extraction pipeline 400, P corresponds to an unstructured business policy, I corresponds to an interpretation of unstructured information of P, B corresponds to a business problem associated with the I, S corresponds to a solution of B, E corresponds to an evaluation of S, and C corresponds to an acceptability criterion for S=C. In accordance with these rules, the information extraction pipeline 400 can proceed as follows. At 402, for a given P, extract a set of possible interpretations of information I(i . . . n). At 404, for each Ii, determine a S that I provides to B, represented as S(B, I). At 406, evaluate the S that I provides to B is through E, represented as E(S(B,I)). At 408, it is determined whether E(S(B,I) satisfies C. If yes, then at 410 the interpretation Ii can be accepted. If no, then at 412, the interpretation Ii can be rejected.

Figure 5:
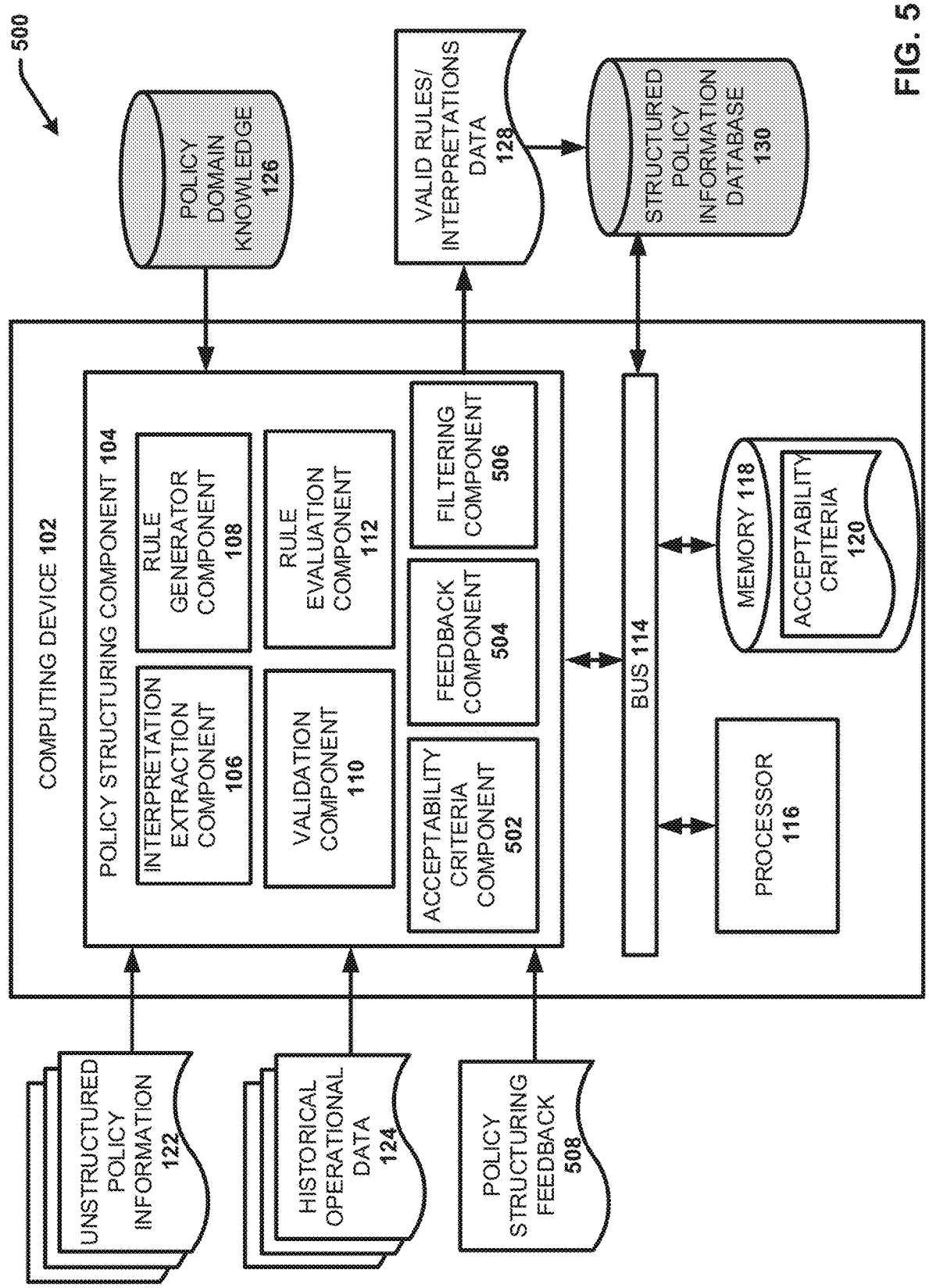
FIG. 5 illustrates a block diagram of another example, non-limiting system that facilitates extracting structured policy rules from unstructured policy documents in accordance with one or more embodiments of the disclosed subject matter.

FIG. 5 illustrates a block diagram of another example, non-limiting system 500 that facilitates extracting structured policy rules from unstructured policy documents in accordance with one or more embodiments of the disclosed subject matter. System 500 can include same or similar features as system 100 with the addition of acceptability criteria component 502, feedback component 504, filtering component 506 and policy structuring feedback 508. Repetitive description of like elements employed in respective embodiments is omitted for sake of brevity.

The acceptability criteria component 502 can facilitate generating the acceptability criteria 120 used by the rule evaluation component 112 to determine or select valid policy rule/requirement interpretations. For example, in some embodiments, the acceptability criteria can be manually defined, such as by an entity that drafted or facilitated drafting the policy, an entity that facilitates regulating or enforcing the policy, an administrator associated with reviewing the policy and the like. In accordance with these embodiments, the acceptability criteria component 502 can facilitates receiving manual input selecting or defining the defined acceptability criteria. In other embodiments, the acceptability criteria component 502 determine the acceptability criteria based on the historical operational data 124, the unstructured policy information 122 and/or the policy domain knowledge data 126 knowledge using one or more machine learning techniques (e.g., supervised or unsupervised techniques, one or more deep learning techniques, one or more neural network-based techniques and the like.

The feedback component 504 can facilitate receiving and applying policy structuring feedback 508 associated with one or more operations of the interpretation extraction component 106, the rule generator component 108, the validation component 110, the rule evaluation component 112 and/or the acceptability criteria component. In this regard, the feedback component 504 can receive feedback (identified in system 500 as policy structuring feedback 508) to control and/or adapt one or more operations of the interpretation extraction component 106, the rule generator component, the validation component 10 and/or the rule evaluation component 112. The policy structuring feedback 508 can be received for example from a system administrator, from an artificial intelligence engine, from another computing entity, or another suitable entity.

For example, in various embodiments, the feedback component 504 can facilitate providing a system administrator with the outputs of interpretation extraction component 106 (e.g., the extracted structured interpretations of a policy rule), the outputs of the rule generator component 108, (e.g., the algorithmic forms of a structured policy interpretation), the outputs of the validation component 110, (e.g., the results/solutions of the algorithmic rules as applied to the historical operational data 124), and the outputs of the rule evaluation component 112 (e.g., the valid interpretations data 128). The system administrator can further provide the feedback component 504 with policy structuring feedback based on one or more of these outputs that can be verify the outputs, identify issues with the outputs, identify corrections to the outputs, identify changes to the outputs, and the like.

For instance, the feedback component 504 can facilitate receiving user expertise to verify and prioritize business criteria to validate the structured candidate interpretations, assist in the rule/algorithm building and the like. In another example, in some implementations, the feedback component 504 can receive feedback information regarding a desired output of the structured candidate policy interpretations. The filtering component 506 can further filter the structured candidate policy interpretations based on feedback. For example, the policy structuring feedback 508 can provide information selecting or identifying a subset of the unstructured policy information 122 for evaluating, a type of the unstructured policy information 122 for evaluating, and the like. For instance, in one embodiment, the policy structuring feedback 508 can identify and/or include information indicating areas of the unstructured policy information 122 that most impactful on FWA or ROI. The policy structuring feedback 508 can further direct the policy structuring component 104 to focus analysis on these specified areas of the policy. Based on this feedback, the filtering component 506 can filter the interpretations extracted by the interpretation extraction component 106 based on one or more of these criteria (e.g., filter interpretations based on those impacting FWA, those impacting ROI, etc.). Alternatively, based on historical the historical operational data 124, the interpretation extraction component 106 can learn (e.g., using one or more machine learning techniques) how to prioritize the interpretations according to one or more preferred business criteria (e.g., ROI, FWA, etc.).

Figure 6:
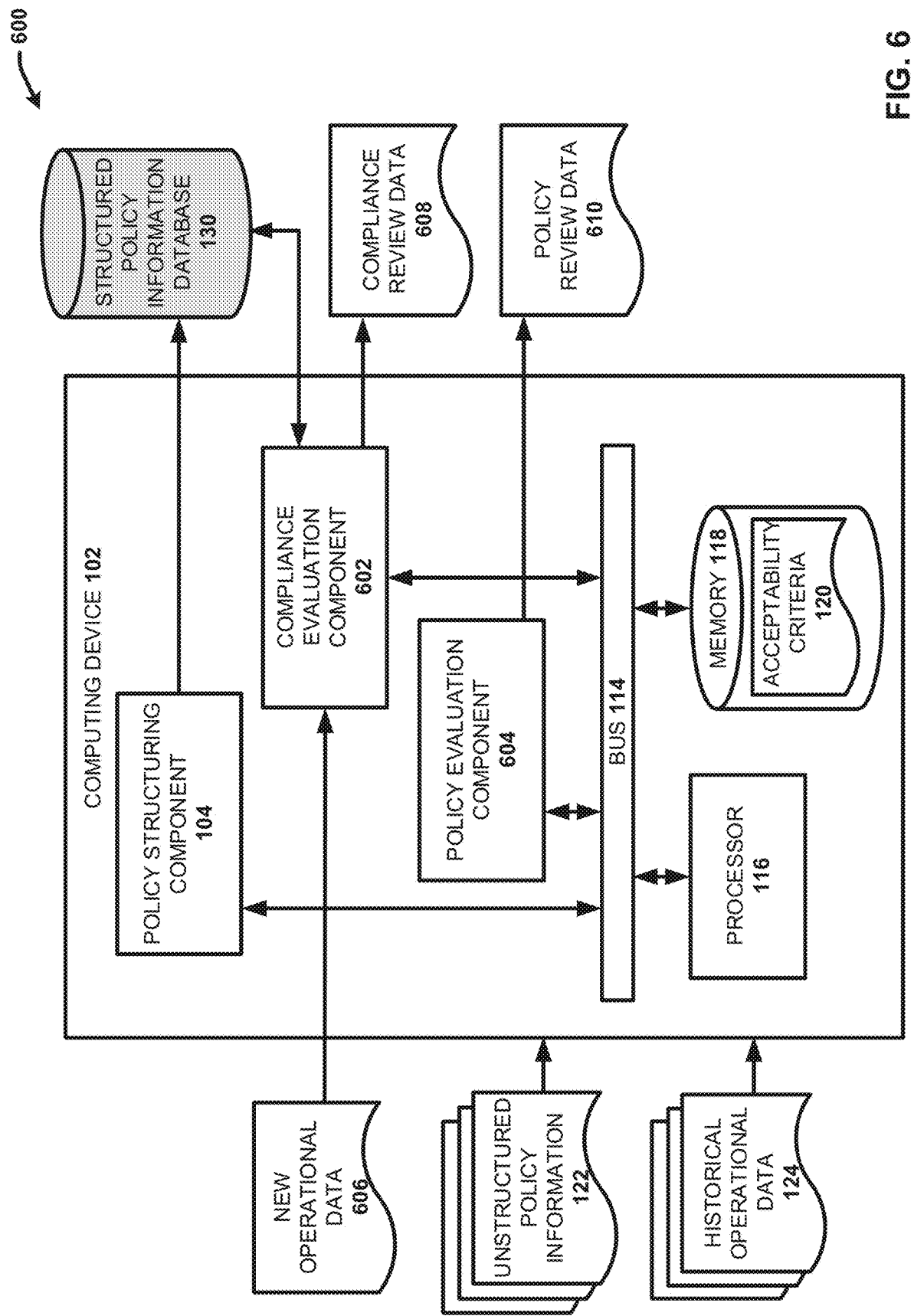
FIG. 6 illustrates a block diagram of an example, non-limiting system that evaluating compliance with a business policy using structured policy rules extracted from unstructured policy documents defining the business policy in accordance with one or more embodiments of the disclosed subject matter.

FIG. 6 illustrates a block diagram of an example, non-limiting system 600 that evaluating compliance with a business policy using structured policy rules extracted from unstructured policy documents defining the business policy in accordance with one or more embodiments of the disclosed subject matter. System 600 can include same or similar features and functionalities as system 100 and system 500 with the addition of new operational data 606, compliance evaluation component 602, policy evaluation component 605, compliance review data 608 and policy review data 610. Repetitive description of like elements employed in respective embodiments is omitted for sake of brevity.

The compliance evaluation component 602 can employ the structured policy information included in the structured policy information database 130 to facilitate evaluating compliance with the operational policy in association with continued operations of the enterprise for which the policy is based. For example, the compliance evaluation component 602 can receive new operational data 606 regarding one or more operations of the enterprise (e.g., in real-time as the operations are being performed, in an evaluation report, in a submitted claim, etc.), and apply the structured policy information to determine whether one or more of the operations comply or fail to comply with the policy. The compliance evaluation component 602 can further generate compliance review data 608 based on the evaluation that can include information identifying whether one or more operations comply with the policy or whether (and optionally why) the one or more operations fail to comply with the policy.

For instance, in an embodiment in which the enterprise comprises an insurance organization and wherein the operational policy defines an insurance claim policy of the insurance organization, the new operational data 606 can include newly submitted claims. According to this example, the compliance evaluation component that evaluates the received insurance claims using the structured policy information included in the structured policy information database 130 to determine whether the received insurance claims violate the insurance claim policy. The compliance evaluation component 602 can further generate compliance review data 608 based on the evaluation that can include information identifying whether a claim complies with the policy or whether (and optionally why) the claim fails to comply with the policy. In some implementations, the compliance evaluation component 602 can automatically accept or reject claims based on a determination as to whether they comply or fail to comply with the structured policy information.

In addition to the processing functions provided by the policy structuring component, and the compliance evaluation component 602, the policy evaluation component 604 can further evaluate a policy in its totality to facilitate optimize the policy with respect to defined goals of the organization for which the policy is based. In this regard, the policy evaluation component 604 can review the unstructured policy information 122, the results/solutions generated by the validation component 110, the valid rule information provided in the structured policy information database 130, the historical operational data 124 and/or the compliance review data 608 to provide a holistic review of the policy regarding including various types of information that reflects whether and to what degree he policy is achieving the goals of the business. The information generated by the policy evaluation component 604 can be provided to another device or entity for further review to facilitate optimizing the policy and/or the performance of the business. This information is represented in system 600 as policy review data 610.

For example, in some implementations the policy evaluation component 604 can evaluate the unstructured policy information 122, the results/solutions generated by the validation component 110, the valid rule information provided in the structured policy information database 130, the historical operational data 124 and/or the compliance review data 608, to determine or infer policy rules that are regularly violated, policy rules that conflict with one another, policy rules that have the greatest impact on a specific goal (e.g., minimizing FWA, increasing return on investment (ROI)), and the like. For example, with respect to an insurance policy, the policy evaluation component 604 can determine or infer information regarding what business rules have the most impact for claims auditing and what business rules are most likely to uncover issues of FWA. The policy evaluation component 604 can also determine information regarding how (e.g., to what degree) a particular policy rule is applicable to operations of the policy based on the historical operational data 124.

In another example, the policy evaluation component 604 can determine or infer, what policy rules are not currently substantiated by historical operational data (e.g., based on a set of interpretations of a policy rule wherein none of the interpretations are supported by the historical operational data 124). The policy evaluation component 604 can also determine or infer information regarding policy rules that are rarely enforced or otherwise least likely to be covered. The policy evaluation component 604 can also determine or infer areas of operation where policy rules are missing or otherwise deficient, etc. For example, the policy evaluation component can identify various operations in the historical data that are not regulated or governed by identified policy rules.

Figure 7:
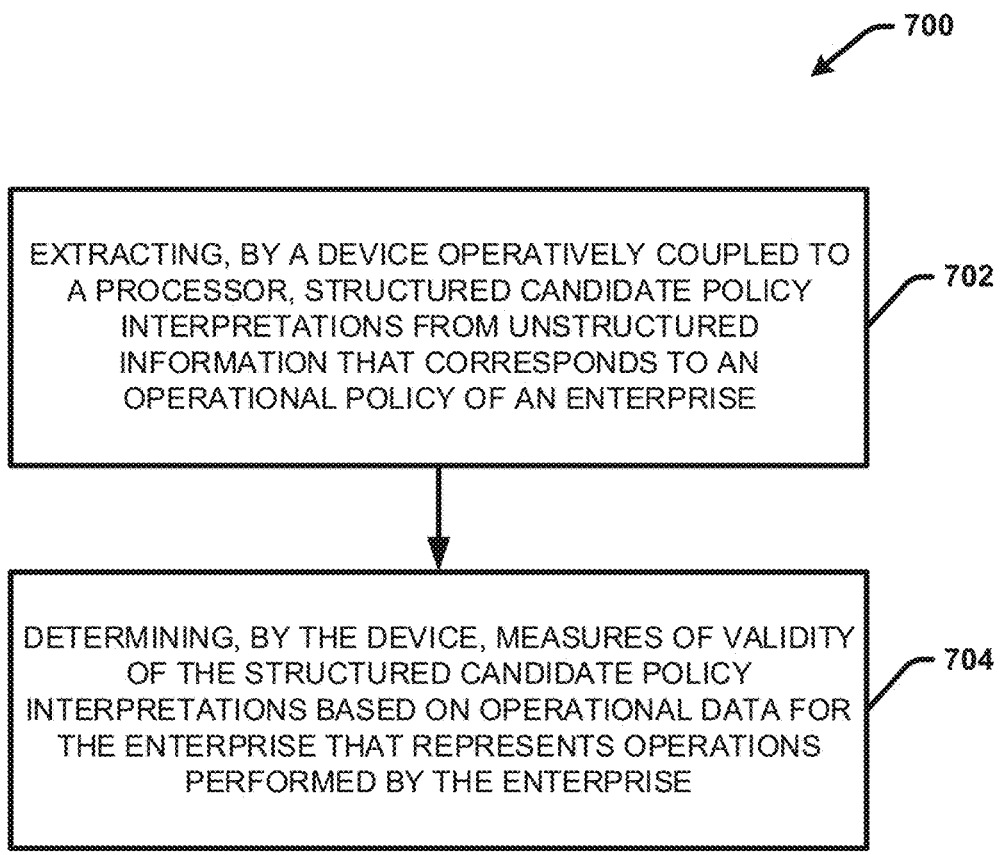
FIG. 7 provides another high-level flow diagram of an example computer-implemented process for extracting structured policy rules from unstructured policy documents in accordance with one or more embodiments of the disclosed subject matter.

FIG. 7 provides another high-level flow diagram of an example computer-implemented process 700 for extracting structured policy rules from unstructured policy documents in accordance with one or more embodiments of the disclosed subject matter. Repetitive description of like elements employed in respective embodiments is omitted for sake of brevity.

At 702, a device operatively coupled to a processor (e.g., computing device 102), extracts structured candidate policy interpretations from unstructured information that corresponds to an operational policy of an enterprise (e.g., via interpretation extraction component 106). At 704, the device, determines measures of validity of the structured candidate policy interpretations based on operational data for the enterprise that represents operations performed by the enterprise (e.g., via the validation component 110).

Figure 8:
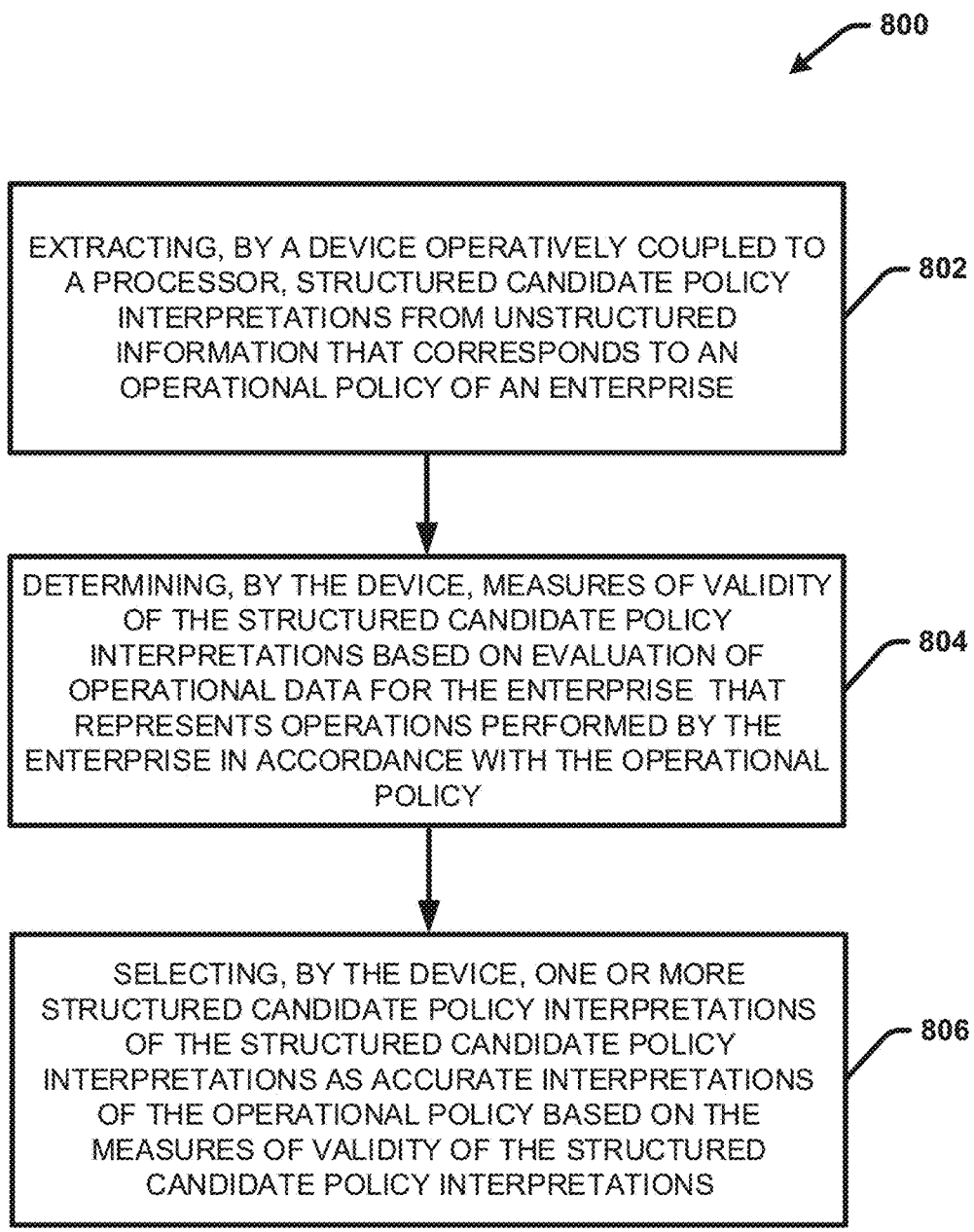
FIG. 8 provides another high-level flow diagram of an example computer-implemented process for extracting structured policy rules from unstructured policy documents in accordance with one or more embodiments of the disclosed subject matter.

FIG. 8 provides another high-level flow diagram of an example computer-implemented process 800 for extracting structured policy rules from unstructured policy documents in accordance with one or more embodiments of the disclosed subject matter. Repetitive description of like elements employed in respective embodiments is omitted for sake of brevity.

At 802, a device operatively coupled to a processor (e.g., computing device 102), extracts structured candidate policy interpretations from unstructured information that corresponds to an operational policy of an enterprise (e.g., via interpretation extraction component 106). At 804, the device, determines measures of validity of the structured candidate policy interpretations based on operational data for the enterprise that represents operations performed by the enterprise in accordance with the operational policy (e.g., via the validation component 110). At 806, the device selects one or more structured candidate policy interpretations of the structured candidate policy interpretations as accurate interpretations of the operational policy based on the measures of validity of the structured candidate policy interpretations (e.g., via rule evaluation component 112).

Figure 9:
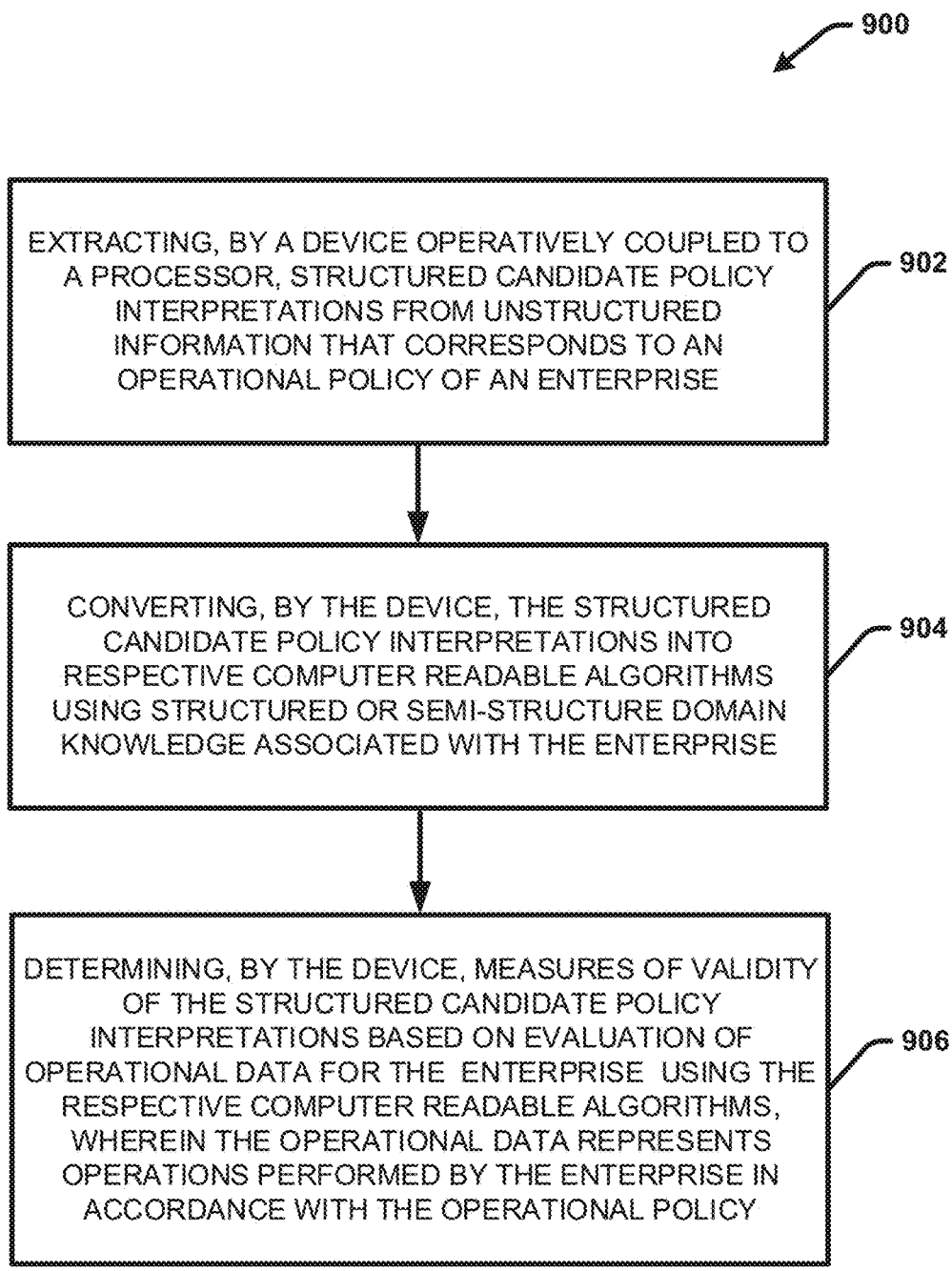
FIG. 9 provides another high-level flow diagram of an example computer-implemented process for extracting structured policy rules from unstructured policy documents in accordance with one or more embodiments of the disclosed subject matter.

FIG. 9 provides another high-level flow diagram of an example computer-implemented process 900 for extracting structured policy rules from unstructured policy documents in accordance with one or more embodiments of the disclosed subject matter. Repetitive description of like elements employed in respective embodiments is omitted for sake of brevity.

At 902, a device operatively coupled to a processor (e.g., computing device 102), extracts structured candidate policy interpretations from unstructured information that corresponds to an operational policy of an enterprise (e.g., via interpretation extraction component 106). At 904, the device, converts the structured candidate policy interpretations into respective computer readable algorithms using structured or semi-structure domain knowledge associated with the enterprise (e.g., via rule generator component 108). At 906, the device determines measures of validity of the structured candidate policy interpretations based on evaluation of operational data for the enterprise using the respective computer readable algorithms, wherein the operational data represents operations performed by the enterprise in accordance with the operational policy (e.g., via validation component 110).

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the entity's computer, partly on the entity's computer, as a stand-alone software package, partly on the entity's computer and partly on a remote computer or entirely on the remote computer or server. In the latter scenario, the remote computer can be connected to the entity's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 10, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 10:
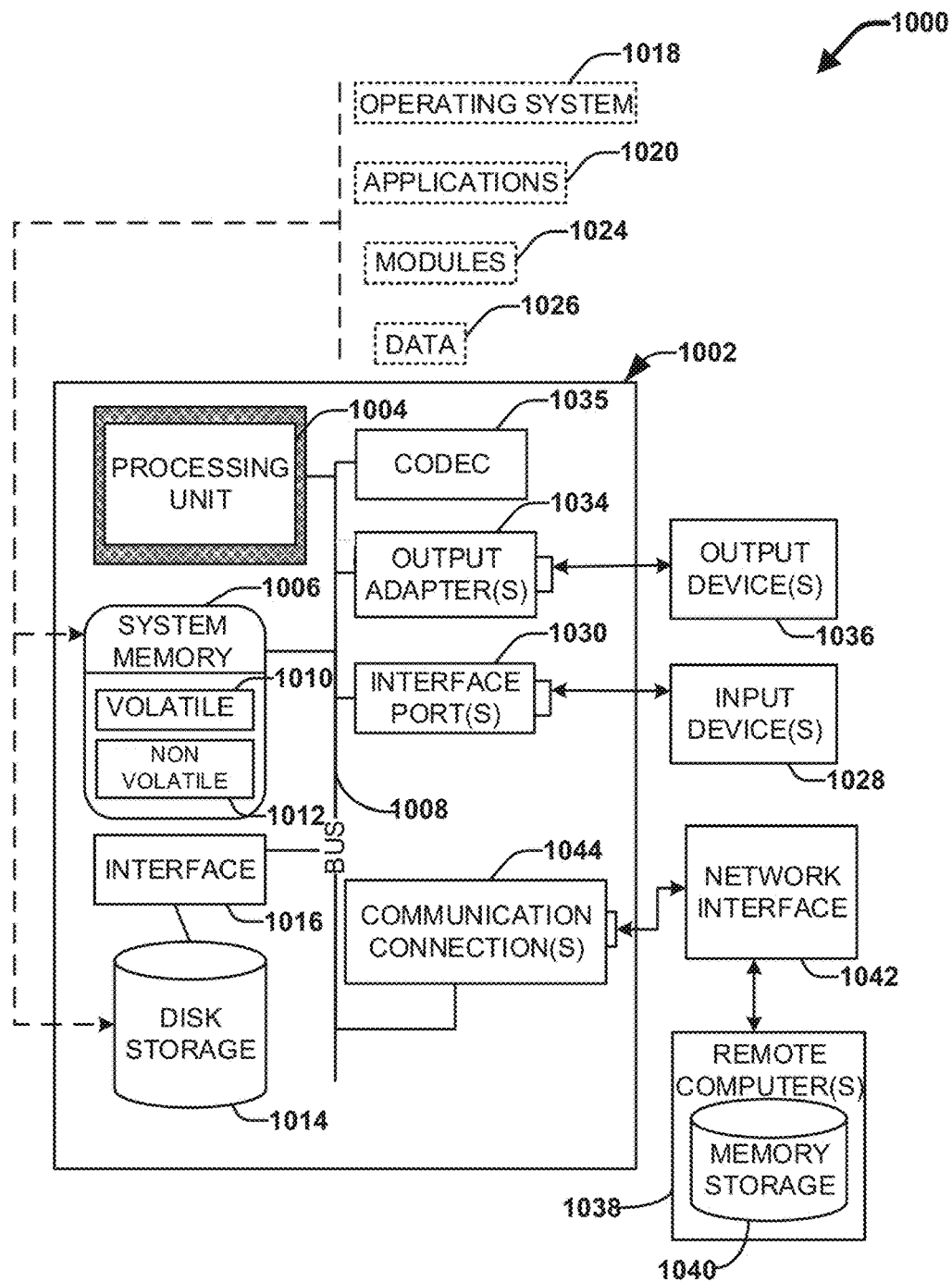
FIG. 10 illustrates a block diagram of an example, non-limiting operating environment in which one or more embodiments described herein can be facilitated.

With reference to FIG. 10, an example environment 1000 for implementing various aspects of the claimed subject matter includes a computer 1002. The computer 1002 includes a processing unit 1004, a system memory 1006, a codec 1035, and a system bus 1008. The system bus 1008 couples system components including, but not limited to, the system memory 1006 to the processing unit 1004. The processing unit 1004 can be any of various available processors. Dual microprocessors and other multiprocessor architectures also can be employed as the processing unit 1004.

The system bus 1008 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13104), and Small Computer Systems Interface (SCSI).

The system memory 1006 includes volatile memory 1010 and non-volatile memory 1012, which can employ one or more of the disclosed memory architectures, in various embodiments. The basic input/output system (BIOS), containing the basic routines to transfer information between elements within the computer 1002, such as during start-up, is stored in non-volatile memory 1012. In addition, according to present innovations, codec 1035 can include at least one of an encoder or decoder, wherein the at least one of an encoder or decoder can consist of hardware, software, or a combination of hardware and software. Although, codec 1035 is depicted as a separate component, codec 1035 can be contained within non-volatile memory 1012. By way of illustration, and not limitation, non-volatile memory 1012 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1012 can employ one or more of the disclosed memory devices, in at least some embodiments. Moreover, non-volatile memory 1012 can be computer memory (e.g., physically integrated with computer 1002 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1010 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1002 can also include removable/non-removable, volatile/non-volatile computer storage medium. FIG. 10 illustrates, for example, disk storage 1014. Disk storage 1014 includes, but is not limited to, devices like a magnetic disk drive, solid state disk (SSD), flash memory card, or memory stick. In addition, disk storage 1014 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1014 to the system bus 1008, a removable or non-removable interface is typically used, such as interface 1016. It is appreciated that disk storage 1014 can store information related to an entity. Such information might be stored at or provided to a server or to an application running on an entity device. In one embodiment, the entity can be notified (e.g., by way of output devices. 1036) of the types of information that are stored to disk storage 1014 or transmitted to the server or application. The entity can be provided the opportunity to opt-in or opt-out of having such information collected or shared with the server or application (e.g., by way of input from input device(s) 1028).

It is to be appreciated that FIG. 10 describes software that acts as an intermediary between entities and the basic computer resources described in the suitable operating environment 1000. Such software includes an operating system 1018. Operating system 1018, which can be stored on disk storage 1014, acts to control and allocate resources of the computer 1002. Applications 1020 take advantage of the management of resources by operating system 1018 through program modules 1024, and program data 1026, such as the boot/shutdown transaction table and the like, stored either in system memory 1006 or on disk storage 1014. It is to be appreciated that the claimed subject matter can be implemented with various operating systems or combinations of operating systems.

An entity enters commands or information into the computer 1002 through input device(s) 1028. Input devices 1028 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1004 through the system bus 1008 via interface port(s) 1030. Interface port(s) 1030 include, for example, a serial port, a parallel port, a game port, and a universal serial bus (USB). Output device(s) 1036 use some of the same type of ports as input device(s) 1028. Thus, for example, a USB port can be used to provide input to computer 1002 and to output information from computer 1002 to an output device 1036. Output adapter 1034 is provided to illustrate that there are some output devices 1036 like monitors, speakers, and printers, among other output devices 1036, which require special adapters. The output adapters 1034 include, by way of illustration and not limitation, video and sound cards that provide a means of connection between the output device 1036 and the system bus 1008. It should be noted that other devices or systems of devices provide both input and output capabilities such as remote computer(s) 1038.

Computer 1002 can operate in a networked environment using logical connections to one or more remote computers, such as remote computer(s) 1038. The remote computer(s) 1038 can be a personal computer, a server, a router, a network PC, a workstation, a microprocessor based appliance, a peer device, a smart phone, a tablet, or other network node, and typically includes many of the elements described relative to computer 1002. For purposes of brevity, only a memory storage device 1040 is illustrated with remote computer(s) 1038. Remote computer(s) 1038 is logically connected to computer 1002 through a network interface 1042 and then connected via communication connection(s) 1044. Network interface 1042 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1044 refers to the hardware/software employed to connect the network interface 1042 to the system bus 1008. While communication connection 1044 is shown for illustrative clarity inside computer 1002, it can also be external to computer 1002. The hardware/software necessary for connection to the network interface 1042 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A device, comprising:
   a memory that stores computer executable components;
   a processor that executes the computer executable components stored in the memory, wherein the computer executable components comprise:
      an extraction component that:
         employs natural language processing on one or more unstructured documents to identify unstructured information that define a rule of an operational policy of an enterprise,
         transform the unstructured information into at least one structured representation according to a structured format,
         transform the at least one structured representation into at least one computer readable algorithm that comprises at least one computer executable query; and
      a validation component that:
         executes the at least one computer readable algorithm on historical operational data of the enterprise to generate respective decisions according to the rule,
         compares the respective decisions of the at least one computer readable algorithm to historical decisions made by at least one entity of the enterprise on the historical operational data according to the rule, and
         determines respective measures of validity of the at least one computer readable algorithm based on the comparison, wherein the respective measures of validity represent degrees to which the respective decisions of the at least one computer readable algorithm accurately reflect the historical decisions made by the at least one entity of the enterprise;
      an acceptability criteria component that employs machine learning analysis of the historical operational data to determine a defined acceptability criterion that corresponds to an acceptable operational performance metric, and
      an evaluation component that selects one or more computer readable algorithms of the at least one computer readable algorithm as one or more accurate interpretations of the rule based on the respective measures of validity and the defined acceptability criterion.

2. The device of claim 1, wherein the acceptability criteria component facilitates receiving manual input selecting or defining the defined acceptability criterion.

3. The device of claim 1, wherein the extraction component employs structured or semi-structured domain knowledge to transform the at least one structured representation into the at least one computer readable algorithm.

4. The device of claim 1, wherein the at least one computer readable algorithm comprise at least two at least one computer readable algorithms, and wherein the evaluation component combines the at least two at least one computer readable algorithms to generate a final computer readable algorithm.

5. The device of claim 1, wherein the computer executable components further comprise:
a feedback component that receives feedback information regarding a desired output of the at least one computer readable algorithm; and
a filtering component that filters the at least one computer readable algorithm based on feedback.

6. The device of claim 1, wherein the computer executable components further comprise:
a compliance evaluation component that evaluates compliance with the rule based on the at least one computer readable algorithm, thereby facilitating identification of instances of non-compliance with increased accuracy and efficiency.

7. The device of claim 1, wherein the enterprise comprises an insurance organization and wherein the unstructured information defines an insurance claim policy of the insurance organization, and wherein the computer executable components further comprise:
a compliance evaluation component that evaluates received insurance claims using the at least one computer readable algorithm to determine whether the received insurance claims violate the insurance claim policy.

8. A computer implemented method, comprising:
identifying, by a device operatively coupled to a processor, using natural language processing on one or more unstructured documents, unstructured information that corresponds to a policy rule of an operational policy of an enterprise;
transforming, by the device, the unstructured information into at least one structured representation according to a structured format;
transforming, by the device, the at least one structured representation into at least one computer readable algorithm that comprises at least one computer executable query;
executing, by the device, the at least one computer readable algorithm on historical operational data of the enterprise to generate respective decisions according to the policy rule;
comparing, by the device, the respective decisions generated by the at least one computer readable algorithm to historical decisions made by at least one entity of the enterprise on the historical operational data according to the policy rule; and
determining, by the device, respective measures of validity of the at least one computer readable algorithm based on the comparing, wherein the respective measures of validity represent degrees to which the respective decisions of the at least one computer readable algorithm accurately reflect the historical decisions made by the at least one entity of the enterprise;
employing, by the device, machine learning analysis of the historical operational data to determine a defined acceptability criterion that corresponds to an acceptable operational performance metric; and
selecting, by the device, one or more computer readable algorithms of the at least one computer readable algorithm as one or more accurate interpretations of the policy rule based on the respective measures of validity and the defined acceptability criterion.

9. The computer implemented method of claim 8, further comprising receiving, by the device, manual input selecting or defining the defined acceptability criterion.

10. The computer implemented method of claim 8, further comprising employing, by the device, structured or semi-structured domain knowledge to transform the at least one structured representation into the at least one computer readable algorithm.

11. The computer implemented method of claim 8, wherein the at least one computer readable algorithm comprise at least two at least one computer readable algorithms, and further comprising combining, by the device, the at least two at least one computer readable algorithms to generate a final computer readable algorithm.

12. The computer implemented method of claim 8, further comprising receiving, by the device, feedback information regarding a desired output of the at least one computer readable algorithm.

13. The computer implemented method of claim 12, further comprising filtering, by the device, the at least one computer readable algorithm based on feedback.

14. The computer implemented method of claim 8, further comprising evaluating, by the device, compliance with the policy rule based on the at least one computer readable algorithm, thereby facilitating identification of instances of non-compliance with increased accuracy and efficiency.

15. A computer program product for automated information extraction from unstructured input data, the computer program product comprising a computer readable storage medium having program instructions embodied therewith, the program instructions executable by a processing component to cause the processing component to:
identify, using natural language processing on one or more unstructured documents, unstructured information that corresponds to a rule of an operational policy of an enterprise;
transform the unstructured information into at least one structured representation according to a structured format;
transform the at least one structured representation into at least one computer readable algorithm that comprises at least one computer executable query;
execute the at least one computer readable algorithm on historical operational data of the enterprise to generate respective decisions according to the rule;
compare the respective decisions generated by the at least one computer readable algorithm to historical decisions made by at least one entity of the enterprise on the historical operational data according to the rule; and
determine respective measures of validity of the at least one computer readable algorithm based on the comparison, wherein the respective measures of validity represent degrees to which the respective decisions of the at least one computer readable algorithm accurately reflect the historical decisions made by the at least one entity of the enterprise;
employ machine learning analysis of the historical operational data to determine a defined acceptability criterion that corresponds to an acceptable operational performance metric; and
selecting one or more computer readable algorithms of the at least one computer readable algorithm as one or more accurate interpretations of the rule based on the respective measures of validity and the defined acceptability criterion.

16. The computer program product of claim 15, wherein the program instructions executable by the processing component further cause the processing component to:
receive manual input selecting or defining the defined acceptability criterion.

17. The computer program product of claim 15, wherein the program instructions executable by the processing component further cause the processing component to:
employ structured or semi-structured domain knowledge to transform the at least one structured representation into the at least one computer readable algorithm.

18. The computer program product of claim 15, wherein the at least one computer readable algorithm comprise at least two at least one computer readable algorithms, and the program instructions executable by the processing component further cause the processing component to:
combine the at least two at least one computer readable algorithms to generate a final computer readable algorithm.

19. The computer program product of claim 15, wherein the program instructions executable by the processing component further cause the processing component to:
receive feedback information regarding a desired output of the at least one computer readable algorithm.

20. The computer program product of claim 19, wherein the program instructions executable by the processing component further cause the processing component to:
filter the at least one computer readable algorithm based on feedback.

* * * * *